(12) United States Patent
Prior (10) Patent No.: US 11,083,443 B2
(45) Date of Patent: Aug. 10, 2021

(54) SPECIMEN RETRIEVAL DEVICE

(71) Applicant: Covidien LP, Mansfield, MA (US)

(72) Inventor: Scott J. Prior, Shelton, CT (US)

(73) Assignee: COVIDIEN LP, Mansfield, MA (US)

( * ) Notice: Subject to any disclaimer, the term of this patent is extended or adjusted under 35 U.S.C. 154(b) by 366 days.

(21) Appl. No.: 16/261,865

(22) Filed: Jan. 30, 2019

(65) Prior Publication Data

US 2019/0321018 A1   Oct. 24, 2019

Related U.S. Application Data

(60) Provisional application No. 62/661,874, filed on Apr. 24, 2018.

(51) Int. Cl.
*A61B 17/00* (2006.01)

(52) U.S. Cl.
CPC ............... *A61B 17/00234* (2013.01); *A61B 2017/00287* (2013.01)

(58) Field of Classification Search
CPC .......................................... A61B 2017/00287
See application file for complete search history.

(56) References Cited

U.S. PATENT DOCUMENTS

| | | |
|---|---|---|
| 30,471 A | 10/1860 | Dudley |
| 35,164 A | 5/1862 | Logan et al. |
| 156,477 A | 11/1874 | Bradford |
| 1,609,014 A | 11/1926 | Dowd |
| 3,800,781 A | 4/1974 | Zalucki |
| 4,557,255 A | 12/1985 | Goodman |
| 4,611,594 A | 9/1986 | Grayhack et al. |
| 4,744,363 A | 5/1988 | Hasson |
| 4,790,812 A | 12/1988 | Hawkins, Jr. et al. |
| 4,852,586 A | 8/1989 | Haines |
| 4,927,427 A | 5/1990 | Kriauciunas et al. |
| 4,977,903 A | 12/1990 | Haines |
| 4,991,593 A | 2/1991 | LeVahn |
| 4,997,435 A | 3/1991 | Demeter |
| 5,037,379 A | 8/1991 | Clayman et al. |
| 5,074,867 A | 12/1991 | Wilk |
| 5,084,054 A | 1/1992 | Bencini et al. |

(Continued)

FOREIGN PATENT DOCUMENTS

| | | |
|---|---|---|
| DE | 25796 C | 1/1884 |
| DE | 3542667 A1 | 6/1986 |

(Continued)

OTHER PUBLICATIONS

European Search Report EP 12191639.9 dated Feb. 20, 2013.

(Continued)

*Primary Examiner* — Shaun L David
(74) *Attorney, Agent, or Firm* — Carter, DeLuca & Farrell LLP (57) ABSTRACT

A specimen retrieval device includes a tubular body defining a longitudinal bore, an inner shaft slidably disposed within the longitudinal bore of the tubular body, and a specimen bag affixed to a support mechanism at the distal portion of the inner shaft. In embodiments, the specimen bag has an opening capable of being closed by linkage assembly after placement of tissue therein, but prior to removal of the device from the body.

12 Claims, 12 Drawing Sheets

(56) References Cited

U.S. PATENT DOCUMENTS

| | | | |
|---|---|---|---|
| 5,143,082 A * | 9/1992 | Kindberg | A61B 17/00234 128/DIG. 24 |
| 5,147,371 A | 9/1992 | Washington et al. | |
| 5,176,687 A | 1/1993 | Hasson et al. | |
| 5,190,542 A | 3/1993 | Nakao et al. | |
| 5,190,555 A | 3/1993 | Wetter et al. | |
| 5,190,561 A | 3/1993 | Graber | |
| 5,192,284 A | 3/1993 | Pleatman | |
| 5,192,286 A | 3/1993 | Phan et al. | |
| 5,201,740 A | 4/1993 | Nakao et al. | |
| 5,215,521 A | 6/1993 | Cochran et al. | |
| 5,224,930 A | 7/1993 | Spaeth et al. | |
| 5,234,439 A | 8/1993 | Wilk et al. | |
| 5,279,539 A | 1/1994 | Bohan et al. | |
| 5,312,416 A | 5/1994 | Spaeth et al. | |
| 5,320,627 A | 6/1994 | Sorensen et al. | |
| 5,330,483 A | 7/1994 | Heaven et al. | |
| 5,336,227 A | 8/1994 | Nakao et al. | |
| 5,337,754 A | 8/1994 | Heaven et al. | |
| 5,341,815 A | 8/1994 | Cofone et al. | |
| 5,352,184 A | 10/1994 | Goldberg et al. | |
| 5,354,303 A | 10/1994 | Spaeth et al. | |
| 5,368,545 A | 11/1994 | Schaller et al. | |
| 5,368,597 A | 11/1994 | Pagedas | |
| 5,370,647 A | 12/1994 | Graber et al. | |
| 5,443,472 A | 8/1995 | Li | |
| 5,451,204 A * | 9/1995 | Yoon | A61B 17/00234 600/572 |
| 5,465,731 A | 11/1995 | Bell et al. | |
| 5,480,404 A | 1/1996 | Kammerer et al. | |
| 5,486,182 A | 1/1996 | Nakao et al. | |
| 5,486,183 A | 1/1996 | Middleman et al. | |
| 5,499,988 A | 3/1996 | Espiner et al. | |
| 5,524,633 A | 6/1996 | Heaven et al. | |
| 5,535,759 A | 7/1996 | Wilk | |
| 5,611,803 A | 3/1997 | Heaven et al. | |
| 5,618,296 A | 4/1997 | Sorensen et al. | |
| 5,630,822 A | 5/1997 | Hermann et al. | |
| 5,642,282 A | 6/1997 | Sonehara | |
| 5,643,282 A | 7/1997 | Kieturakis | |
| 5,643,283 A | 7/1997 | Younker | |
| 5,645,083 A | 7/1997 | Essig et al. | |
| 5,647,372 A | 7/1997 | Tovey et al. | |
| 5,649,902 A | 7/1997 | Yoon | |
| 5,658,296 A | 8/1997 | Bates et al. | |
| 5,679,423 A | 10/1997 | Shah | |
| 5,681,324 A | 10/1997 | Kammerer et al. | |
| 5,720,754 A | 2/1998 | Middleman et al. | |
| 5,735,289 A | 4/1998 | Pfeffer et al. | |
| 5,741,271 A | 4/1998 | Nakao et al. | |
| 5,755,724 A | 5/1998 | Yoon | |
| 5,759,187 A | 6/1998 | Nakao et al. | |
| 5,769,794 A | 6/1998 | Conlan et al. | |
| 5,769,848 A * | 6/1998 | Wattanasirichaigoon | A61B 17/29 606/215 |
| 5,782,840 A | 7/1998 | Nakao | |
| 5,785,677 A | 7/1998 | Auweiler | |
| 5,788,709 A | 8/1998 | Riek et al. | |
| 5,792,145 A | 8/1998 | Bates et al. | |
| 5,814,044 A | 9/1998 | Hooven | |
| 5,829,440 A | 11/1998 | Broad, Jr. | |
| 5,836,953 A | 11/1998 | Yoon | |
| 5,853,374 A | 12/1998 | Hart et al. | |
| 5,895,392 A | 4/1999 | Riek et al. | |
| 5,904,690 A | 5/1999 | Middleman et al. | |
| 5,906,621 A | 5/1999 | Secrest et al. | |
| 5,908,429 A | 6/1999 | Yoon | |
| 5,957,884 A | 9/1999 | Hooven | |
| 5,971,995 A | 10/1999 | Rousseau | |
| 5,980,544 A | 11/1999 | Vaitekunas | |
| 5,997,547 A | 12/1999 | Nakao et al. | |
| 6,004,330 A | 12/1999 | Middleman et al. | |
| 6,007,512 A | 12/1999 | Hooven | |
| 6,007,546 A | 12/1999 | Snow et al. | |
| 6,019,770 A * | 2/2000 | Christoudias | A61B 17/00234 604/403 |
| 6,036,681 A | 3/2000 | Hooven | |
| 6,059,793 A | 5/2000 | Pagedas | |
| 6,123,701 A | 9/2000 | Nezhat | |
| 6,152,932 A | 11/2000 | Ternstrom | |
| 6,156,055 A | 12/2000 | Ravenscroft | |
| 6,162,235 A | 12/2000 | Vaitekunas | |
| 6,165,121 A | 12/2000 | Alferness | |
| 6,168,603 B1 | 1/2001 | Leslie et al. | |
| 6,206,889 B1 | 3/2001 | Bennardo | |
| 6,228,095 B1 | 5/2001 | Dennis | |
| 6,258,102 B1 | 7/2001 | Pagedas | |
| 6,264,663 B1 | 7/2001 | Cano | |
| 6,270,505 B1 | 8/2001 | Yoshida et al. | |
| 6,277,083 B1 | 8/2001 | Eggers et al. | |
| 6,280,450 B1 | 8/2001 | McGuckin, Jr. | |
| 6,344,026 B1 | 2/2002 | Burbank et al. | |
| 6,348,056 B1 | 2/2002 | Bates et al. | |
| 6,350,266 B1 | 2/2002 | White et al. | |
| 6,350,267 B1 | 2/2002 | Stefanchik | |
| 6,368,328 B1 | 4/2002 | Chu et al. | |
| 6,383,195 B1 | 5/2002 | Richard | |
| 6,383,196 B1 | 5/2002 | Leslie et al. | |
| 6,383,197 B1 | 5/2002 | Conlon et al. | |
| 6,387,102 B2 | 5/2002 | Pagedas | |
| 6,406,440 B1 | 6/2002 | Stefanchik | |
| 6,409,733 B1 | 6/2002 | Conlon et al. | |
| 6,419,639 B2 | 7/2002 | Walther et al. | |
| 6,447,523 B1 | 9/2002 | Middleman et al. | |
| 6,471,659 B2 | 10/2002 | Eggers et al. | |
| 6,506,166 B1 | 1/2003 | Hendler et al. | |
| 6,508,773 B2 | 1/2003 | Burbank et al. | |
| 6,537,273 B1 * | 3/2003 | Sosiak | A61B 18/14 606/170 |
| 6,547,310 B2 | 4/2003 | Myers | |
| 6,589,252 B2 | 7/2003 | McGuckin, Jr. | |
| 6,752,811 B2 | 6/2004 | Chu et al. | |
| 6,755,779 B2 | 6/2004 | Vanden Hoek et al. | |
| 6,780,193 B2 | 8/2004 | Leslie et al. | |
| 6,805,699 B2 | 10/2004 | Shimm | |
| 6,840,948 B2 | 1/2005 | Albrecht et al. | |
| 6,872,211 B2 | 3/2005 | White et al. | |
| 6,887,255 B2 | 5/2005 | Shimm | |
| 6,958,069 B2 | 10/2005 | Shipp et al. | |
| 6,971,988 B2 | 12/2005 | Orban, III | |
| 6,994,696 B2 | 2/2006 | Suga | |
| 7,014,648 B2 | 3/2006 | Ambrisco et al. | |
| 7,018,373 B2 | 3/2006 | Suzuki | |
| 7,052,454 B2 | 5/2006 | Taylor | |
| 7,052,501 B2 | 5/2006 | McGuckin, Jr. | |
| 7,090,637 B2 | 8/2006 | Danitz et al. | |
| 7,115,125 B2 | 10/2006 | Nakao et al. | |
| 7,270,663 B2 | 9/2007 | Nakao | |
| 7,273,488 B2 | 9/2007 | Nakamura et al. | |
| 7,410,491 B2 | 8/2008 | Hopkins et al. | |
| 7,547,310 B2 | 6/2009 | Whitfield | |
| 7,618,437 B2 | 11/2009 | Nakao | |
| 7,670,346 B2 | 3/2010 | Whitfield | |
| 7,722,626 B2 | 5/2010 | Middleman et al. | |
| 7,762,959 B2 | 7/2010 | Bilsbury | |
| 7,785,251 B2 | 8/2010 | Wilk | |
| 7,819,121 B2 | 10/2010 | Amer | |
| 7,837,612 B2 | 11/2010 | Gill et al. | |
| RE42,050 E | 1/2011 | Richard | |
| 7,892,242 B2 | 2/2011 | Goldstein | |
| 8,016,771 B2 | 9/2011 | Orban, III | |
| 8,057,485 B2 | 11/2011 | Hollis et al. | |
| 8,075,567 B2 | 12/2011 | Taylor et al. | |
| 8,097,001 B2 | 1/2012 | Nakao | |
| 8,152,820 B2 | 4/2012 | Mohamed et al. | |
| 8,172,772 B2 | 5/2012 | Zwolinski et al. | |
| 8,206,401 B2 | 6/2012 | Nakao | |
| 8,337,510 B2 | 12/2012 | Rieber et al. | |
| 8,343,031 B2 | 1/2013 | Gertner | |
| 8,348,827 B2 | 1/2013 | Zwolinski | |
| 8,388,630 B2 | 3/2013 | Teague et al. | |
| 8,409,112 B2 | 4/2013 | Wynne et al. | |
| 8,409,216 B2 | 4/2013 | Parihar et al. | |

(56) References Cited

U.S. PATENT DOCUMENTS

| | | |
|---|---|---|
| 8,409,217 B2 | 4/2013 | Parihar et al. |
| 8,414,596 B2 | 4/2013 | Parihar et al. |
| 8,419,749 B2 | 4/2013 | Shelton, IV et al. |
| 8,425,533 B2 | 4/2013 | Parihar et al. |
| 8,430,826 B2 | 4/2013 | Uznanski et al. |
| 8,435,237 B2 | 5/2013 | Bahney |
| 8,444,655 B2 | 5/2013 | Parihar et al. |
| 8,579,914 B2 | 11/2013 | Menn et al. |
| 8,585,712 B2 | 11/2013 | O'Prey et al. |
| 8,591,521 B2 | 11/2013 | Cherry et al. |
| 8,652,147 B2 | 2/2014 | Hart |
| 8,696,683 B2 | 4/2014 | LeVert |
| 8,721,658 B2 | 5/2014 | Kahle et al. |
| 8,734,464 B2 | 5/2014 | Grover et al. |
| 8,777,961 B2 | 7/2014 | Cabrera et al. |
| 8,795,291 B2 | 8/2014 | Davis et al. |
| 8,821,377 B2 | 9/2014 | Collins |
| 8,827,968 B2 | 9/2014 | Taylor et al. |
| 8,870,894 B2 | 10/2014 | Taylor et al. |
| 8,906,035 B2 | 12/2014 | Zwolinski et al. |
| 8,906,036 B2 | 12/2014 | Farascioni |
| 8,956,370 B2 | 2/2015 | Taylor et al. |
| 8,968,329 B2 | 3/2015 | Cabrera |
| 2002/0068943 A1 | 6/2002 | Chu et al. |
| 2002/0082516 A1 | 6/2002 | Stefanchik |
| 2003/0073970 A1 | 4/2003 | Suga |
| 2003/0100909 A1 | 5/2003 | Suzuki |
| 2003/0100919 A1 | 5/2003 | Hopkins et al. |
| 2003/0199915 A1 | 10/2003 | Shimm |
| 2003/0216773 A1 | 11/2003 | Shimm |
| 2004/0097960 A1 | 5/2004 | Terachi et al. |
| 2004/0138587 A1 | 7/2004 | Lyons |
| 2005/0085808 A1 | 4/2005 | Nakao |
| 2005/0165411 A1 | 7/2005 | Orban |
| 2005/0267492 A1 | 12/2005 | Poncet et al. |
| 2006/0030750 A1 | 2/2006 | Amer |
| 2006/0052799 A1 | 3/2006 | Middleman et al. |
| 2006/0058776 A1 | 3/2006 | Bilsbury |
| 2006/0169287 A1 | 8/2006 | Harrison et al. |
| 2006/0200169 A1 | 9/2006 | Sniffin |
| 2006/0200170 A1 | 9/2006 | Aranyi |
| 2006/0229639 A1 | 10/2006 | Whitfield |
| 2006/0229640 A1 | 10/2006 | Whitfield |
| 2007/0016224 A1 | 1/2007 | Nakao |
| 2007/0016225 A1 | 1/2007 | Nakao |
| 2007/0073251 A1 | 3/2007 | Zhou et al. |
| 2007/0088370 A1 | 4/2007 | Kahle et al. |
| 2007/0135780 A1 | 6/2007 | Pagedas |
| 2007/0135781 A1 | 6/2007 | Hart |
| 2007/0186935 A1 | 8/2007 | Wang et al. |
| 2008/0188766 A1 | 8/2008 | Gertner |
| 2008/0221587 A1 | 9/2008 | Schwartz |
| 2008/0221588 A1* | 9/2008 | Hollis ............ A61B 17/00234 606/114 |
| 2008/0234696 A1* | 9/2008 | Taylor ............ A61B 17/00234 606/114 |
| 2008/0300621 A1 | 12/2008 | Hopkins et al. |
| 2008/0312496 A1 | 12/2008 | Zwolinski |
| 2009/0043315 A1 | 2/2009 | Moon |
| 2009/0082779 A1 | 3/2009 | Nakao |
| 2009/0182292 A1 | 7/2009 | Egle et al. |
| 2009/0192510 A1 | 7/2009 | Bahney |
| 2009/0240238 A1 | 9/2009 | Grodrian et al. |
| 2010/0000471 A1 | 1/2010 | Hibbard |
| 2010/0152746 A1* | 6/2010 | Ceniccola ........ A61B 17/00234 606/114 |
| 2011/0087235 A1* | 4/2011 | Taylor ............ A61B 17/00234 606/114 |
| 2011/0184311 A1 | 7/2011 | Parihar et al. |
| 2011/0184434 A1 | 7/2011 | Parihar et al. |
| 2011/0184435 A1 | 7/2011 | Parihar et al. |
| 2011/0184436 A1 | 7/2011 | Shelton, IV et al. |
| 2011/0190779 A1 | 8/2011 | Gell et al. |
| 2011/0190781 A1 | 8/2011 | Collier et al. |
| 2011/0190782 A1* | 8/2011 | Fleming ......... A61B 17/00234 606/114 |
| 2011/0264091 A1 | 10/2011 | Koppleman et al. |
| 2011/0299799 A1 | 12/2011 | Towe |
| 2012/0046667 A1 | 2/2012 | Cherry et al. |
| 2012/0083795 A1 | 4/2012 | Fleming et al. |
| 2012/0083796 A1* | 4/2012 | Grover ............ A61B 17/00234 606/114 |
| 2012/0083797 A1* | 4/2012 | Cabrera ............ A61B 17/00234 606/114 |
| 2012/0203241 A1 | 8/2012 | Williamson, IV |
| 2013/0023895 A1 | 1/2013 | Saleh |
| 2013/0103042 A1 | 4/2013 | Davis |
| 2013/0103043 A1* | 4/2013 | Cabrera ............ A61B 17/0293 606/114 |
| 2013/0116592 A1 | 5/2013 | Whitfield |
| 2013/0190773 A1 | 7/2013 | Carlson |
| 2013/0218170 A1 | 8/2013 | Uznanski et al. |
| 2013/0245636 A1 | 9/2013 | Jansen |
| 2013/0274758 A1 | 10/2013 | Young et al. |
| 2013/0325025 A1 | 12/2013 | Hathaway et al. |
| 2014/0046337 A1 | 2/2014 | O'Prey et al. |
| 2014/0058403 A1 | 2/2014 | Menn et al. |
| 2014/0180303 A1 | 6/2014 | Duncan et al. |
| 2014/0222016 A1 | 8/2014 | Grover et al. |
| 2014/0236110 A1 | 8/2014 | Taylor et al. |
| 2014/0243865 A1 | 8/2014 | Swayze et al. |
| 2014/0249541 A1 | 9/2014 | Kahle et al. |
| 2014/0276913 A1 | 9/2014 | Tah et al. |
| 2014/0303640 A1 | 10/2014 | Davis et al. |
| 2014/0309656 A1 | 10/2014 | Gal et al. |
| 2014/0330285 A1 | 11/2014 | Rosenblatt et al. |
| 2014/0350567 A1 | 11/2014 | Schmitz et al. |
| 2014/0371759 A1 | 12/2014 | Hartoumbekis |
| 2014/0371760 A1 | 12/2014 | Menn |
| 2015/0018837 A1 | 1/2015 | Sartor et al. |
| 2015/0045808 A1 | 2/2015 | Farascioni |
| 2016/0213362 A1* | 7/2016 | Holsten ............ A61B 17/00234 |
| 2017/0020500 A1* | 1/2017 | Taylor ............. A61B 17/00234 |
| 2017/0215904 A1 | 8/2017 | Wassef et al. |

FOREIGN PATENT DOCUMENTS

| | | |
|---|---|---|
| DE | 8435489 U1 | 8/1986 |
| DE | 4204210 A1 | 8/1992 |
| DE | 19624826 A1 | 1/1998 |
| EP | 0947166 A2 | 10/1999 |
| EP | 1685802 A1 | 8/2006 |
| EP | 1707126 A1 | 10/2006 |
| EP | 2005900 A2 | 12/2008 |
| EP | 2184014 A2 | 5/2010 |
| EP | 2436313 A2 | 4/2012 |
| EP | 2474270 A2 | 7/2012 |
| EP | 2583629 A2 | 4/2013 |
| FR | 1272412 A | 9/1961 |
| GB | 246009 A | 1/1926 |
| WO | 9315675 A1 | 8/1993 |
| WO | 9509666 A1 | 4/1995 |
| WO | 01335831 A1 | 5/2001 |
| WO | 2004002334 A1 | 1/2004 |
| WO | 2004112571 A2 | 12/2004 |
| WO | 2005112783 A1 | 12/2005 |
| WO | 2006110733 | 10/2006 |
| WO | 2007048078 A1 | 4/2007 |
| WO | 2007048085 A2 | 4/2007 |
| WO | 2008114234 A2 | 9/2008 |
| WO | 2009149146 A1 | 12/2009 |
| WO | 2011090862 A2 | 7/2011 |
| WO | 2014134285 A1 | 9/2014 |
| WO | 2015134888 A1 | 9/2015 |
| WO | 2017189442 A1 | 11/2017 |

OTHER PUBLICATIONS

European Search Report EP 11250837.9 dated Sep. 10, 2013.
European Search Report EP 11250838.7 dated Sep. 10, 2013.
European Search Report EP 13170118.7 dated Dec. 5, 2013.
European Search Report EP 12165852 dated Jun. 20, 2012.

(56) References Cited

OTHER PUBLICATIONS http://www.biomaterials.org/week/bio17.cfm, definition and examples of hydrogels.
European Search Report EP 12150271 dated Jan. 14, 2013.
European Search Report EP 12193450 dated Feb. 27, 2013.
European Search Report EP 12189517.1 dated Mar. 6, 2013.
European Search Report EP 12158873 dated Jul. 19, 2012.
European Search Report EP 11250836 dated Sep. 12, 2013.
European Search Report dated Feb. 12, 2019 issued in EP Application No. 18208634.
Extended European Search Report issued in corresponding Appl. No. EP 19170619.1dated Sep. 19, 2019 (8 pages).

\* cited by examiner

SPECIMEN RETRIEVAL DEVICE

CROSS-REFERENCE TO RELATED APPLICATION

This application claims the benefit of and priority to U.S. Provisional Patent Application No. 62/661,874 filed Apr. 24, 2018, the entire disclosure of which is incorporated by reference herein.

TECHNICAL FIELD

The present disclosure relates generally to surgical apparatuses for use in minimally invasive surgical procedures, such as endoscopic and/or laparoscopic procedures and, more particularly, the present disclosure relates to specimen retrieval devices including an opening that may be closed after placement of a tissue specimen therein.

BACKGROUND

Minimally invasive surgery, such as endoscopic surgery, reduces the invasiveness of surgical procedures. Endoscopic surgery involves surgery through body walls, for example, viewing and/or operating on the ovaries, uterus, gall bladder, bowels, kidneys, appendix, etc. There are many common endoscopic surgical procedures, including arthroscopy, laparoscopy, gastroentroscopy and laryngobronchoscopy, just to name a few. In these procedures, trocars are utilized for creating incisions through which the endoscopic surgery is performed. Trocar tubes or cannula devices are extended into and left in place in the abdominal wall to provide access for endoscopic surgical tools. A camera or endoscope is inserted through a trocar tube to permit visual inspection and magnification of a body cavity. The surgeon can then perform diagnostic and/or therapeutic procedures at the surgical site with the aid of specialized instrumentation, such as forceps, graspers, cutters, applicators, and the like, which are designed to fit through additional cannulas.

When removing certain tissues from the body cavity, for example tumor tissue, it is important that the tumor tissue does not come into contact with healthy or uninvolved tissue. If tumor tissue or tissue parts have to be removed, they may be introduced into an "extraction bag," also referred to herein as a "specimen bag," at the site where the tumor or diseased tissue has been detached from the surrounding tissue, after which the specimen bag is withdrawn from the body, thereby minimizing contact of the diseased tissue with healthy tissue.

Improved specimen bags for use in minimally invasive surgical procedures remain desirable.

SUMMARY

Specimen retrieval devices in accordance with the present disclosure include a tubular body defining a longitudinal bore, the tubular body having a proximal portion, a distal portion, and a hand grip supported on the proximal portion of the tubular body; an inner shaft having a proximal portion, a distal portion, an actuation handle supported on the proximal portion of the inner shaft, and a support member extending from a distal portion of the inner shaft; a specimen bag supported on the support member at the distal portion of the inner shaft, the specimen bag including a body defining an opening that is opened and closed by a band adjacent at least a portion of the opening; and a linkage assembly including a linkage rod having a proximal portion, a distal portion, a longitudinal body that extends between the proximal portion and the distal portion, and a pair of linkage bars extending from the distal portion of the longitudinal body of the linkage rod, the pair of linkage bars each attached to the band adjacent at least a portion of the opening by biasing means rotatable around an axis transverse to the specimen bag, the biasing members pivoting the band adjacent at least a portion of the opening to close the opening when the linkage rod is moved in a closing direction.

In embodiments, the support member includes a pair of resilient fingers which support the specimen bag and open the open end of the specimen bag in a deployed state.

In some embodiments, the resilient fingers are positioned adjacent the open end of the specimen bag to open the specimen bag when the specimen retrieval device is in the deployed state.

In other embodiments, the specimen bag is furled about the inner shaft in a non-deployed state.

In embodiments, the biasing means include torsion springs.

In some embodiments, moving the linkage rod in a closing direction includes proximally pulling the linkage rod.

In embodiments, the proximal portion of the linkage rod has a ring configuration.

In some embodiments, the linkage rod extends proximally from the tubular body.

In other embodiments, the proximal portion of each of the inner shaft and the linkage rod extends proximally from the tubular body.

Methods for using the specimen retrieval device of the present disclosure are also provided. In embodiments, these methods include introducing a tubular body of a specimen retrieval device through a body opening into a body cavity; introducing an inner shaft having a proximal portion and a distal portion through a longitudinal bore of the tubular body; introducing a linkage rod having a proximal portion and a distal portion through the longitudinal bore of the tubular body; moving the inner shaft including a support member within the longitudinal bore of the tubular body to position a specimen bag supported on the support member within the body cavity; placing a tissue specimen into the specimen bag through an opening in the specimen bag; moving the linkage rod including a linkage assembly attached to the specimen bag adjacent an opening of the specimen bag to permit biasing members connecting the linkage assembly to a band adjacent the opening of the specimen bag to close the opening of the specimen bag within the body cavity; and removing the specimen retrieval device from the body cavity.

In embodiments, the method further includes breaking up the tissue specimen in the specimen bag prior to removing the specimen retrieval device from the body cavity.

In some embodiments, moving the linkage rod occurs by proximally pulling the linkage rod.

BRIEF DESCRIPTION OF THE DRAWINGS

Embodiments of the presently disclosed specimen retrieval devices are described hereinbelow with reference to the drawings wherein.

DETAILED DESCRIPTION OF THE EMBODIMENTS

The present disclosure provides specimen retrieval devices for use in minimally invasive surgical procedures. As used herein with reference to the present disclosure, minimally invasive surgical procedures encompass laparoscopic procedures, arthroscopic procedures, and endoscopic procedures, and refer to procedures utilizing scopes or similar devices having relatively narrow operating portions capable of insertion through a small incision in the skin.

The aspects of the present disclosure may be modified for use with various methods for retrieving tissue specimens during minimally invasive surgical procedures, sometimes referred to herein as minimally invasive procedures. Examples of minimally invasive procedures include, for example, cholecystectomies, appendectomies, nephrectomies, colectomies, splenectomies, and the like.

The presently disclosed specimen retrieval devices will now be described in detail with reference to the drawings in which like reference numerals designate identical or corresponding elements in each of the several views. In this description, the term "proximal" is used generally to refer to that portion of the device that is closer to a clinician, while the term "distal" is used generally to refer to that portion of the device that is farther from the clinician. The term "clinician" is used generally to refer to medical personnel including doctors, surgeons, nurses, and support personnel.

Referring to FIGS. 1-13, and initially with reference to FIGS. 1-6, the specimen retrieval device 10 in accordance with an exemplary embodiment of the present disclosure includes a tubular body 12 having a proximal portion 16 and a distal portion 18, and defines a longitudinal bore 14 that extends between the proximal portion 16 and the distal portion 18. The tubular body 12 has a hand grip 15 thereon. The specimen retrieval device 10 also includes an inner shaft assembly 20 (FIG. 2) including an inner shaft 22 slidably positioned within the longitudinal bore 14 of the tubular body 12, an actuation handle 25 secured to a proximal portion 24 of the inner shaft 22, and a specimen bag 70 (FIG. 6) supported on a distal portion 26 of the inner shaft 22.

Figure 1:
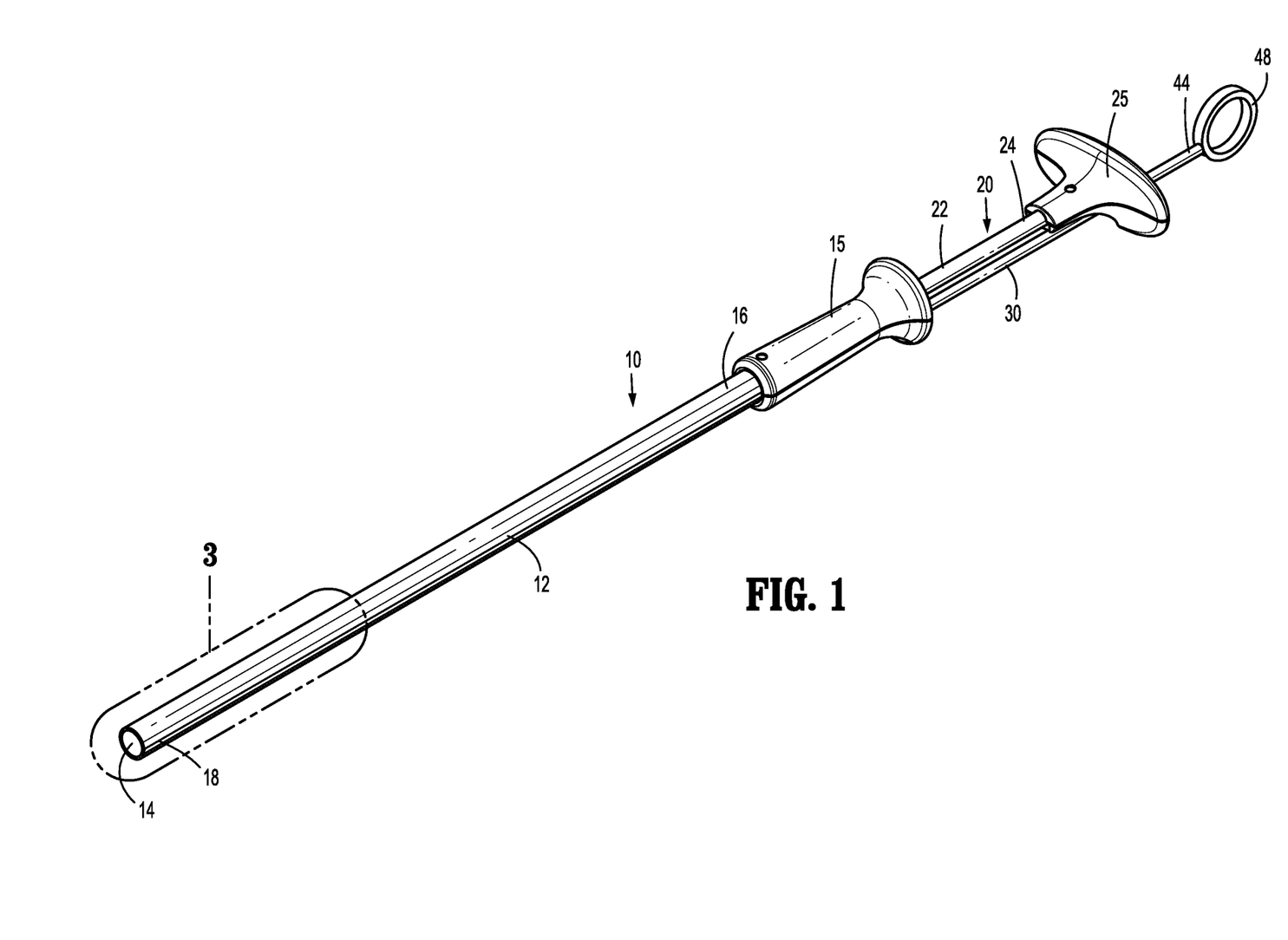
FIG. 1 is a side perspective view of a specimen retrieval device in accordance with an exemplary embodiment of the present disclosure.
Figure 2:
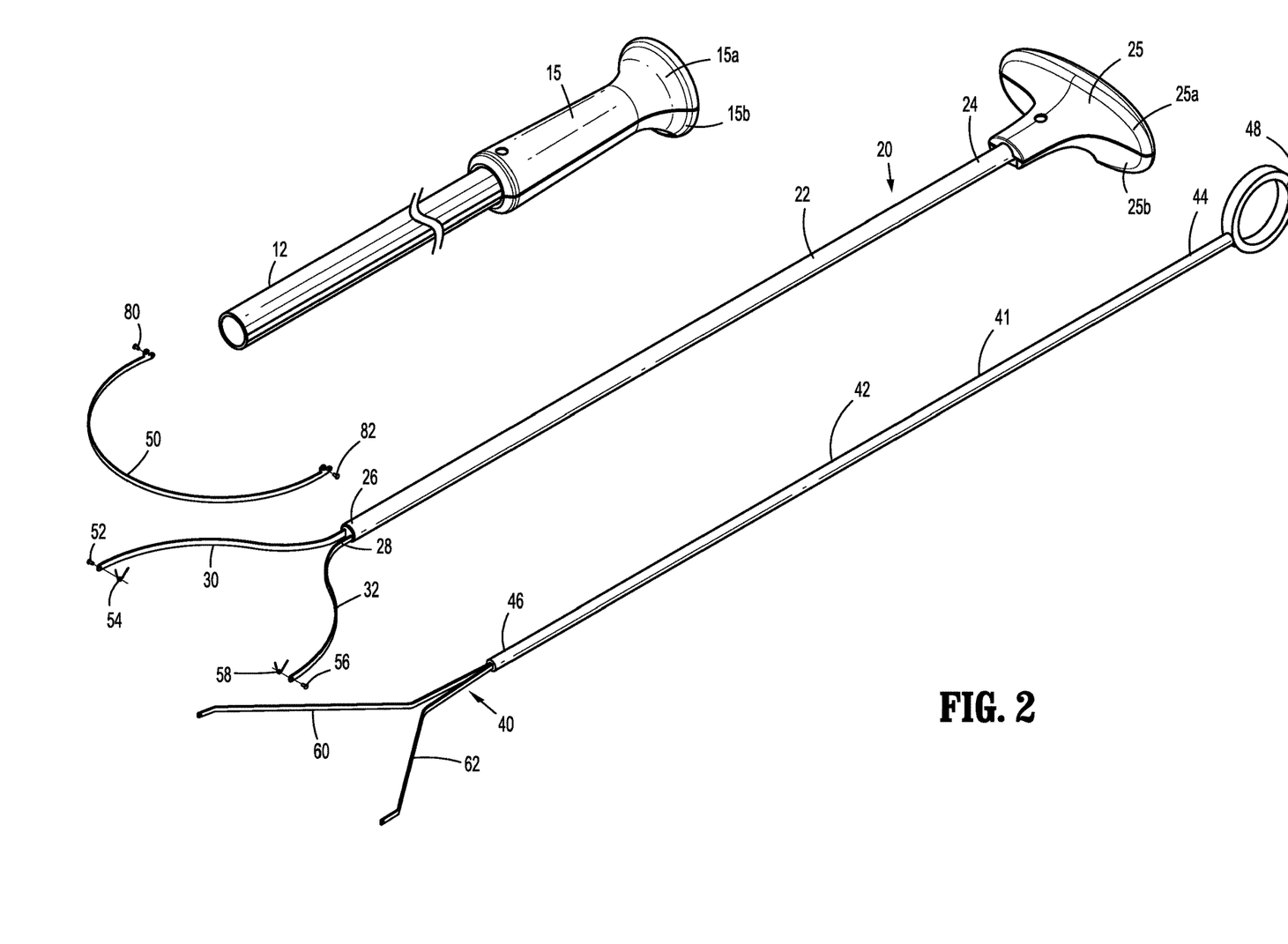
FIG. 2 is an exploded view of the specimen retrieval device shown in FIG. 1.

The hand grip 15 on the tubular body 12 may be formed as a unitary component or, as depicted in FIG. 2, as two separate half components 15a, 15b, that are coupled to one another about the proximal portion of the tubular body 12 by one or more suitable coupling methods (e.g., one or more suitable adhesives). In the latter instance, an indent/detent configuration (not shown) may be utilized to facilitate coupling the two separate half components 15a, 15b to one another.

The actuation handle 25 on the inner shaft 22 may likewise be formed as a unitary component or, in embodiments, as depicted in FIG. 2, as two separate half components 25a, 25b that are coupled to one another by one or more suitable coupling methods (e.g., one or more suitable adhesives).

The specimen retrieval device 10 also includes a linkage rod 41 (FIG. 2) having a proximal portion 44, a distal portion 46, and a longitudinal body 42 that extends between the proximal portion 44 and the distal portion 46. A linkage assembly 40 is supported at the distal portion 46 of the linkage rod 41. As described in greater detail below, the linkage assembly 40 is capable of closing a specimen bag 70 supported on the distal portion of the inner shaft 22. In embodiments, the longitudinal body 42 has a ring 48 at its proximal portion 44 to facilitate manipulation of the linkage rod 41.

In some embodiments, the tubular body 12 may define two separate longitudinal bores (not shown) therein, the first longitudinal bore suitable for passage of the inner shaft 12 therethrough, and the second longitudinal bore suitable for passage of the linkage rod 41 therethrough.

In an assembled configuration, the hand grip 15 and the actuation handle 25 can be manipulated to facilitate manipulation of the specimen retrieval device 10 and the sliding of the inner shaft 22 within the tubular body 12. More specifically, the hand grip 15 can be grasped by the clinician with one hand and the actuation handle 25 can be grasped by the clinician with the other hand to move the inner shaft 22 within the tubular body 12.

The tubular body 12, the inner shaft 22, and/or the linkage rod 41 of the present disclosure are made of biocompatible materials within the purview of those skilled in the art, in embodiments, polymeric materials. For example, the tubular body 12, the inner shaft 22, and/or the linkage rod 41 may be made of thermoplastic polyurethanes sold under the name PELLETHANE®, which offer flexibility and a wide range of hardness. The tubular body 12, the inner shaft assembly 22, and/or the linkage rod 41, for example, may be fabricated from PELLETHANE® 2363-80A, PELLETHANE® 2363-90A, PELLETHANE® 2363-55D, any combination thereof, or any alternatives within the purview of those skilled in the art.

In some embodiments, the tubular body 12, the inner shaft assembly 22, and/or the linkage rod 41, are formed of the same material. In other embodiments, the tubular body 12, the inner shaft assembly 22, and/or the linkage rod 41, are formed of different materials.

Figure 4:
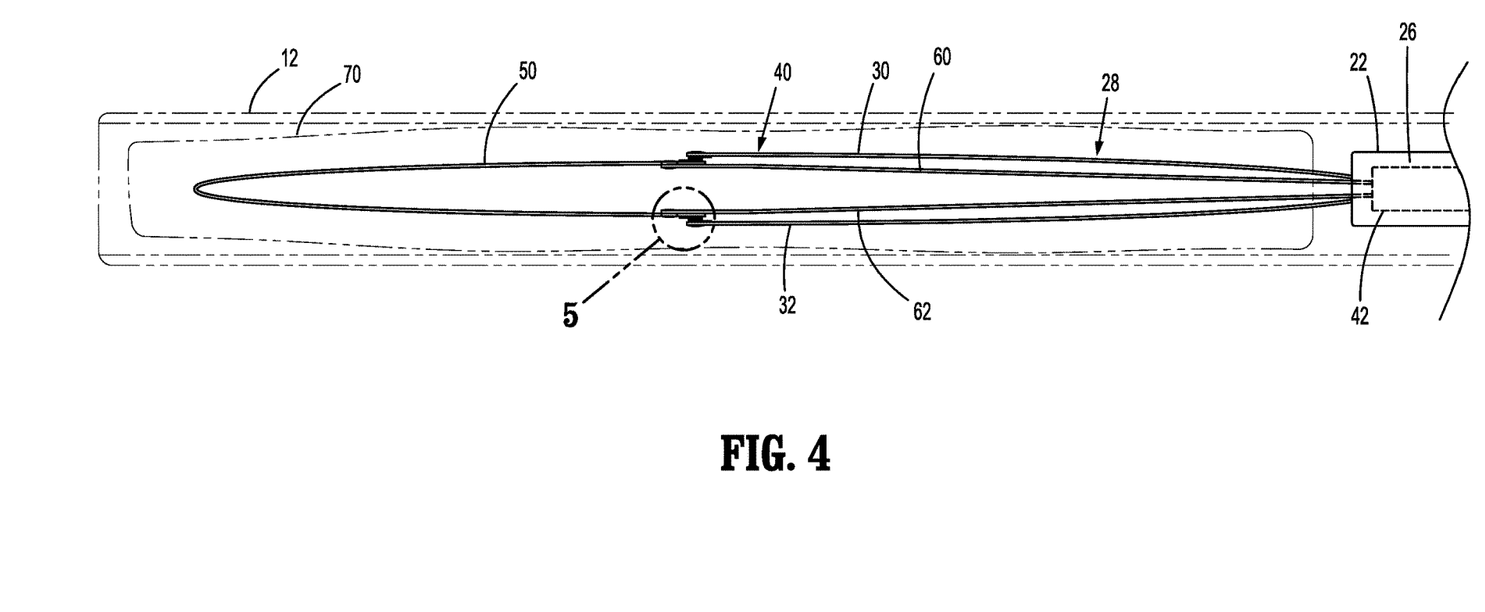
FIG. 4 is a side view of a distal portion of the specimen retrieval device shown in FIG. 3.

The specimen bag 70 (FIG. 6) includes a body 74 having a generally tubular or elongated configuration that is defined by an openable and closable portion (or mouth) 72 and a closed portion 76. The closable portion 72 defines an opening 75. Alternatively, other specimen bag configurations are envisioned. Referring to FIG. 4, the distal portion 26 of the inner shaft 22 is coupled to a support member 28 that is configured to support the specimen bag 70. In embodiments, the support member 28 includes a pair of resilient fingers 30, 32 that extend distally from the distal portion 26 of the inner shaft 22. In embodiments, the resilient fingers 30, 32 can be integrally formed with the distal portion 26 of the inner shaft 22 such as by molding.

Alternatively, a retention pin (not shown) may be used to attach the resilient fingers 30, 32 to the distal portion 26 of the inner shaft 22. The resilient fingers 30, 32 are movable from a spaced non-deformed state (FIG. 6) to a deformed state (FIG. 4) to facilitate placement of the specimen bag 70 into the tubular body 12. The resilient fingers 30, 32 return to the non-deformed state (FIG. 6) when the specimen bag 70 is deployed from the tubular body 12 to open the opening 72 (FIG. 6) of the specimen bag 70, as described below. Alternately, the specimen bag 70 can be supported on the distal portion 26 of the inner shaft 22 using other fastening or securing techniques.

The body 74 of the specimen bag 70 may be made from any suitable biocompatible material (e.g., nylon, urethane, ripstop nylon or latex) capable of forming a flexible collapsible member, or membrane. In embodiments, the material from which the specimen bag is made is resilient, antistatic, pyrogen-free, non-toxic, and sterilizable. In embodiments, materials used to form the tubular body 12 and/or the inner shaft 22 described above may be used to form the specimen bag 70. In other embodiments, the specimen bag 70 is formed of materials that are different from those used to form the tubular body 12 and/or the inner shaft 22. The specimen bag 70 may be opaque or clear.

As depicted in FIGS. 4-7, the resilient fingers 30, 32 are connected to a band 50 which can pivot to close the opening 75 of the specimen bag 70. The band 50 is attached to biasing members, in embodiments at least one torsion spring, which can pivot to move the band 50 and close the opening 75 of the specimen bag 70. The band 50 is attached to one end of the resilient finger 30 by a first retention pin 52 and a first spring 54, and attached to the end of the other resilient finger 32 with a second retention pin 56 and a second spring 58. The first and second springs 54, 58, in embodiments, torsion springs, are rotatable around an axis and pivot in vivo to close the opening 75 of the specimen bag 70.

As depicted in FIG. 2, the linkage assembly 40 includes linkage bars 60, 62 extending from the distal portion 46 of the longitudinal body 42 of the linkage rod 41. The linkage bars 60, 62 hold the specimen bag 70 open in vivo. Proximally pulling the linkage rod 41 in vivo allows the first and second springs 54, 58 to pivot as described above, thereby pivoting the band 50 to close the opening 75 of the specimen bag 70.

Figure 3:
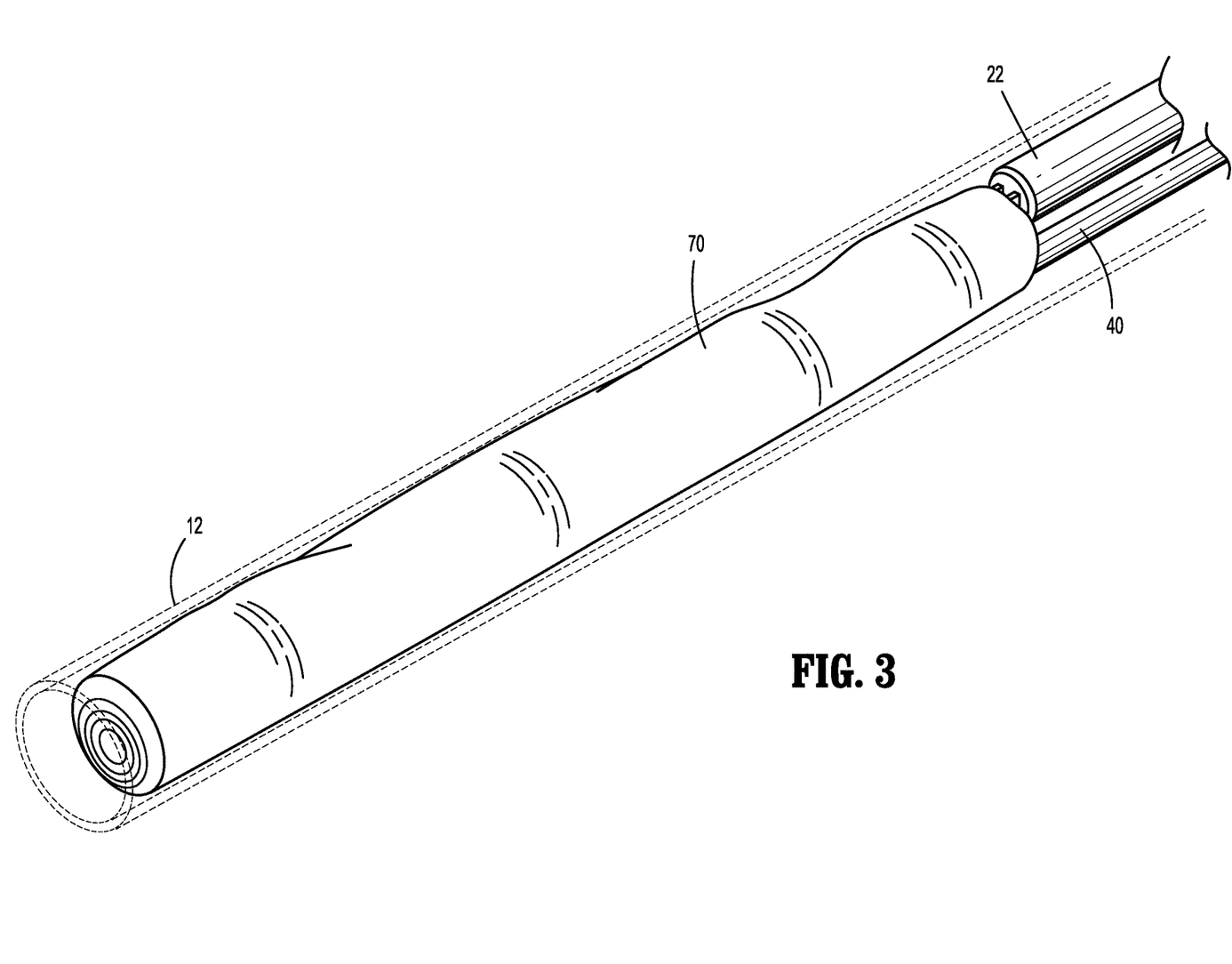
FIG. 3 is an enlarged view of the indicated area of detail shown in FIG. 1.

As depicted in FIG. 3, the specimen bag 70 may be furled about the distal portion 26 of the inner shaft 22 for insertion into the longitudinal bore 14 of the tubular body 12. More specifically, the inner shaft 22 may be rotated either clockwise or counter-clockwise prior to the inner shaft 22 being introduced into the tubular body 12, so that the specimen bag 70 is furled about the support member 28 at the distal portion 26 of the inner shaft 22. Thereafter, the specimen bag 70 can be introduced into the longitudinal bore 14 of the tubular body 12. The specimen retrieval device 10 is then ready to be introduced into a patient. FIG. 3 shows the furled specimen bag 70 after insertion into the tubular body 12 which is shown in phantom.

FIG. 4 is a plan view of the distal portion 18 of the tubular body 12, showing the tubular body 12 and the specimen bag 70 in phantom. The resilient fingers 30, 32, the band 50, and the linkage bars 60, 62 are all depicted within the furled specimen bag 70 (shown in phantom) in a deformed state, which, in turn, is within the tubular body 12 (shown in phantom).

Figure 5:
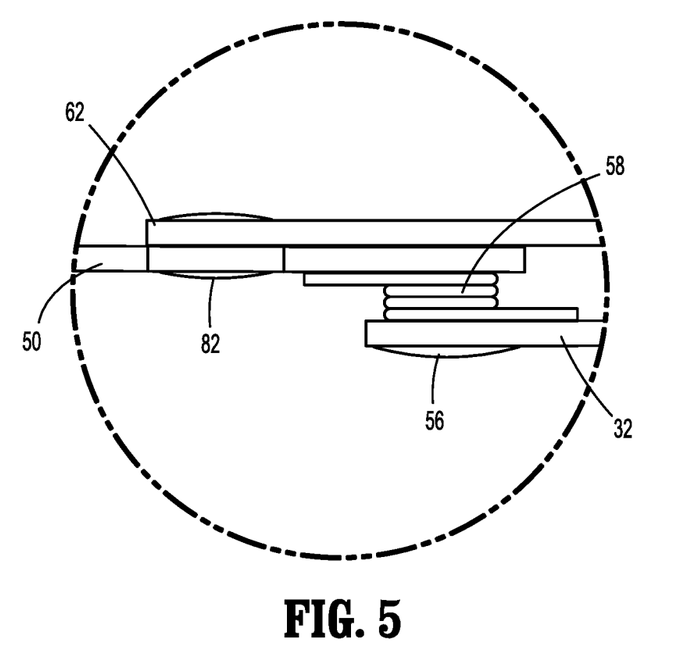
FIG. 5 is an enlarged view of the indicated area of detail shown in FIG. 4.

FIG. 5 shows the connection between resilient finger 32, band 50, and linkage bar 62. As seen in FIG. 5, spring 58 is between resilient finger 32 and band 50. Retention pin 56 holds the resilient finger 32, spring 58, and band 50 together. Retention pin 82 holds linkage bar 62 and band 50 together.

In use, the tubular body 12 of the specimen retrieval device 10 can be inserted through an incision (not shown) with the specimen bag 40 furled about the inner shaft 22 and positioned within the tubular body 12 to position the specimen bag 40 in a body cavity adjacent a surgical site. When the tubular body 12 is properly positioned, the clinician can grip the hand grip 15.

Figure 6:
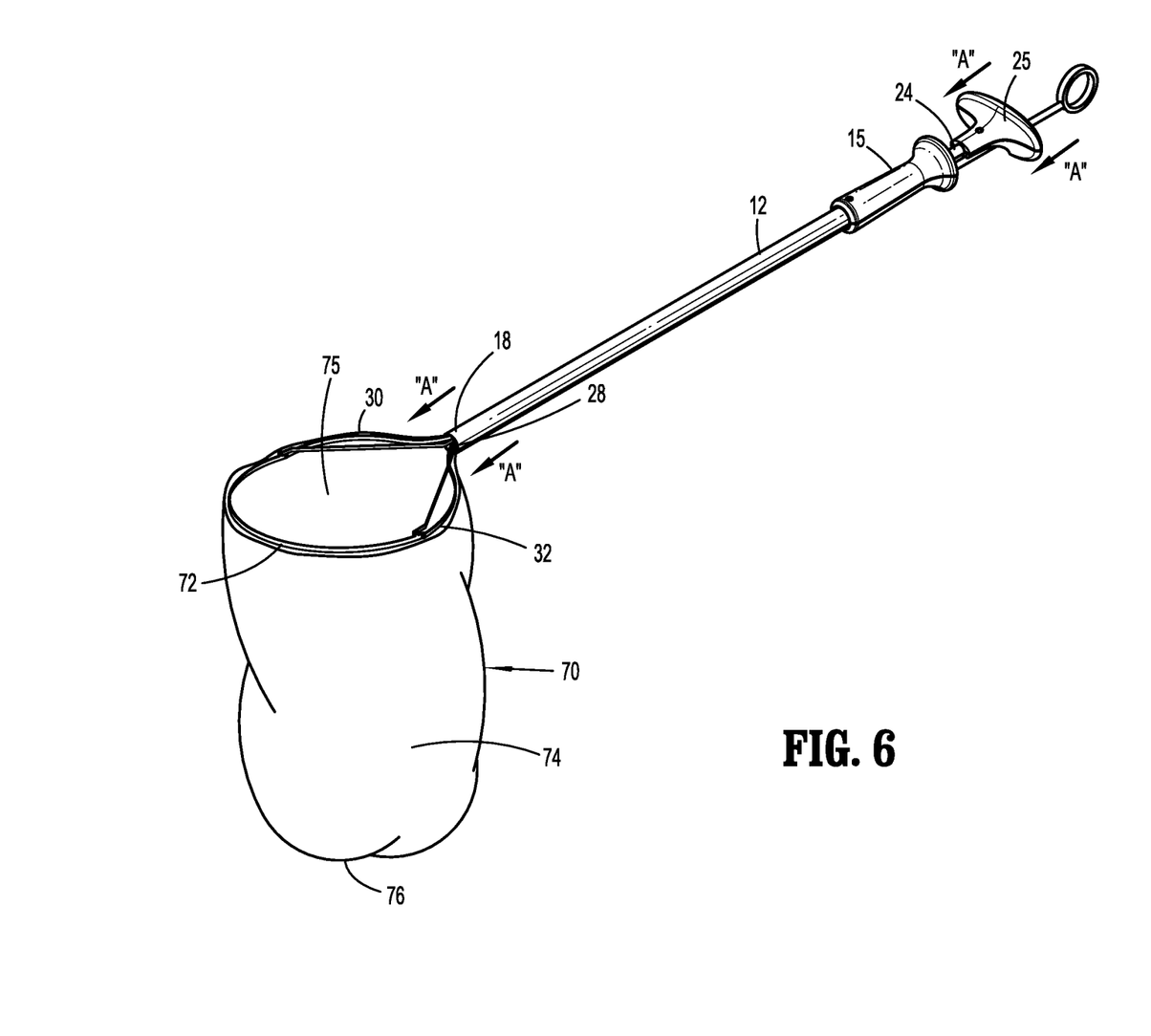
FIG. 6 is a side, perspective view of the specimen retrieval device shown in FIG. 1 with a specimen bag of the specimen retrieval device deployed.

Turning to FIG. 6, the clinician then pushes the actuation handle 25 on the proximal portion 24 of the inner shaft 22 distally in relation to the hand grip 15 and the tubular body 12, in the direction indicated by arrow "A" in FIG. 6, so the support member 28 of the inner shaft 22, including the specimen bag 70, exits the distal portion 18 of the tubular body 12. Once the specimen bag 70 has exited the tubular body 12, the resilient fingers 30, 32 (FIG. 4) return to their non-deformed state, thereby opening the mouth 72 of the specimen bag 70 to ensure the specimen bag 70 is deployed.

When the specimen bag 70 is unfurled, the resilient fingers 30, 32, return to their non-deformed state to open the mouth 72 of the specimen bag 70 so that the specimen bag 70 is in a fully deployed position capable of receiving a tissue specimen "TS" (FIGS. 11 and 12) therein. After the tissue specimen "TS" is received within the specimen bag 40, the specimen retrieval device 40 may then be removed from the body cavity.

Figure 7:
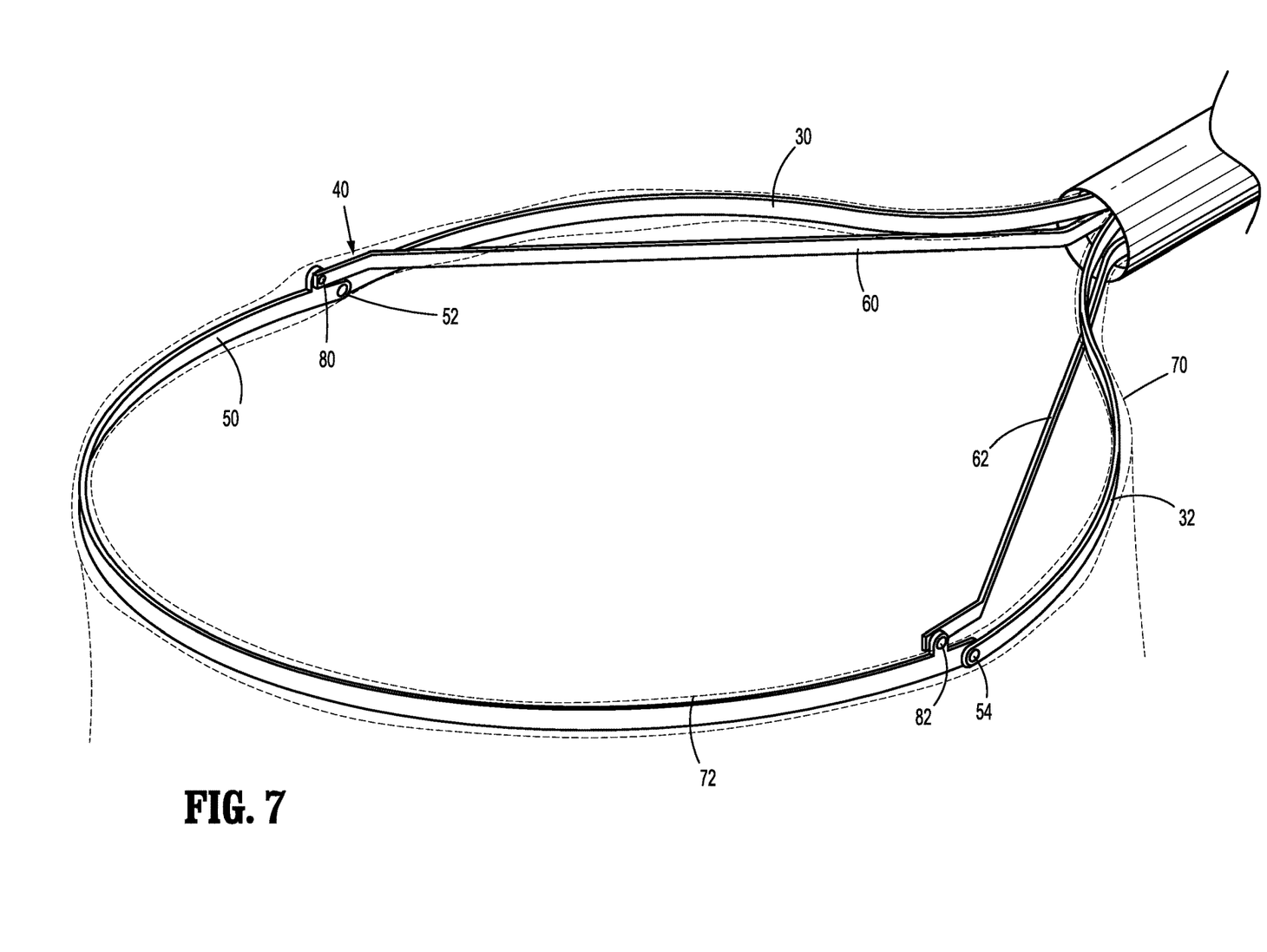
FIG. 7 is an enlarged, side perspective view of the distal portion of the specimen retrieval device shown in FIG. 4 with the specimen bag deployed and the mouth of the specimen bag open.

FIG. 7 shows the deployment of the specimen bag 70 (shown in phantom). As depicted in FIG. 7, the resilient fingers 30, 32 open the mouth 72 of the specimen bag 70. The resilient fingers 30, 32 are attached to the band 50 and the springs (not shown) by the retention pins 52, 56. The band 50, being formed of a flexible material, also expands to form the mouth 72 of the specimen bag 70. The linkage bars 60, 62 pass to the band 50, and are attached thereto by the retention pins 80, and 82.

Figure 8:
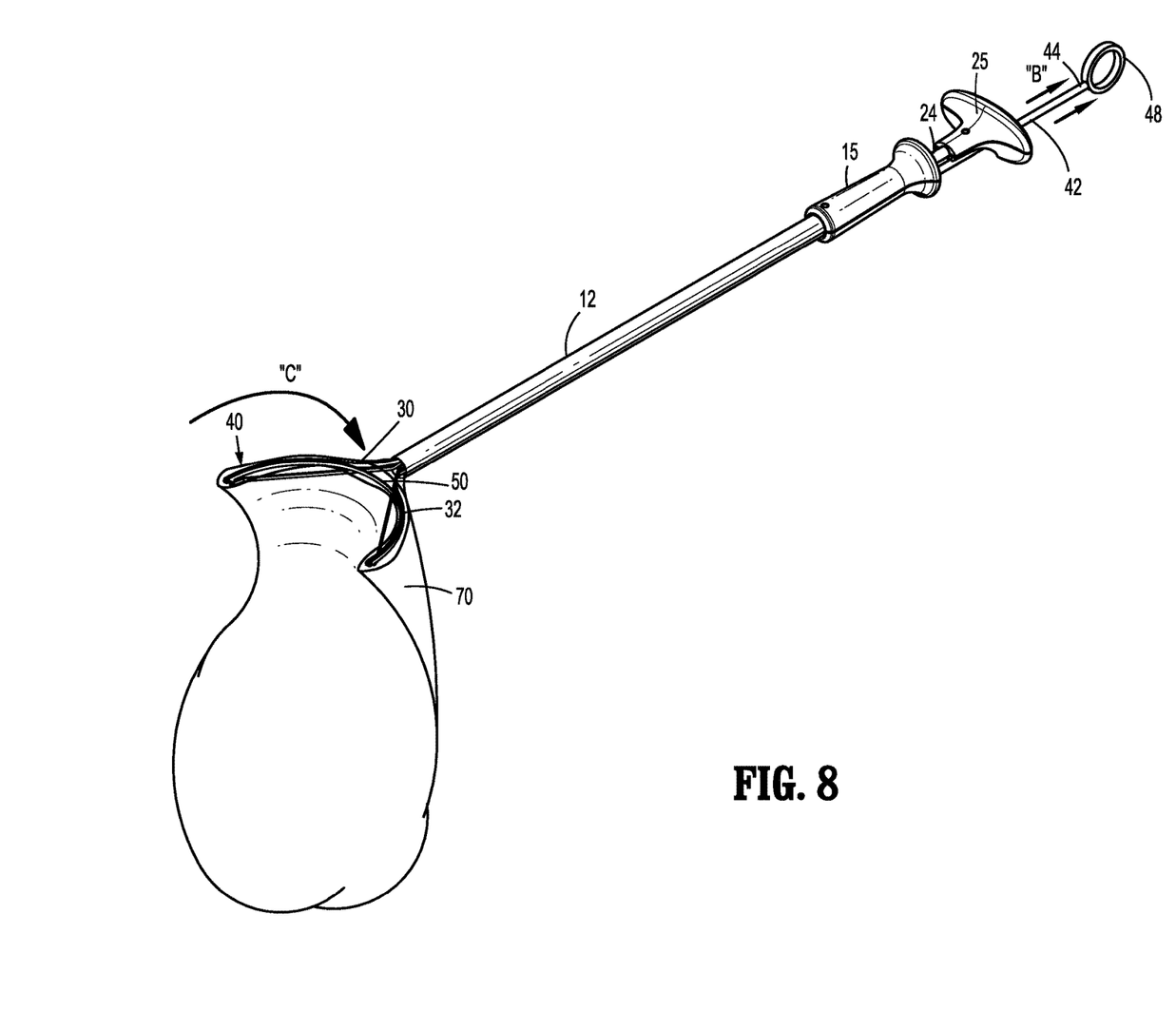
FIG. 8 is a side perspective view of the specimen retrieval device of FIG. 1 showing the closing of the mouth of the specimen bag after deployment from the specimen retrieval device.
Figure 9:
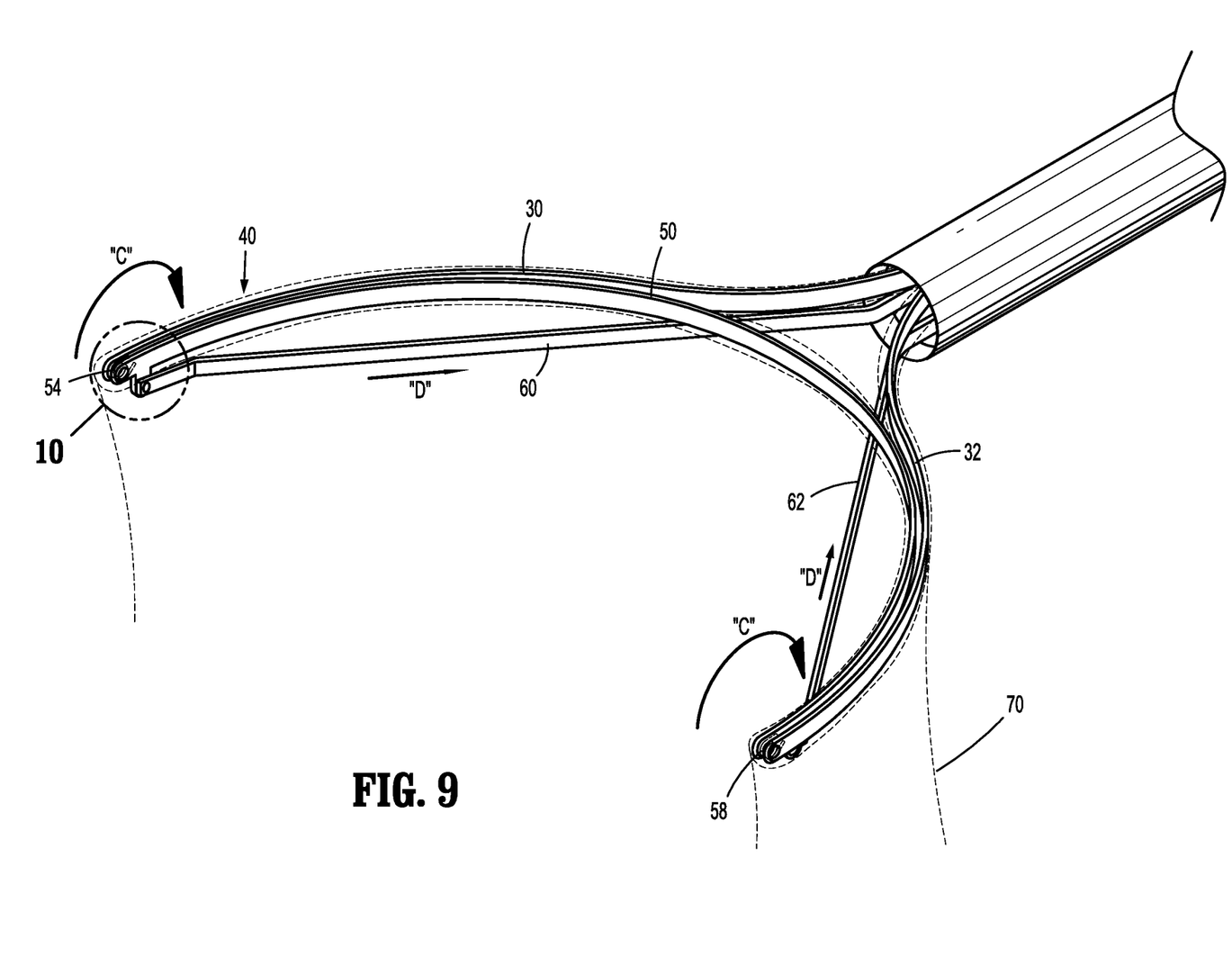
FIG. 9 is an enlarged, side perspective view of the distal portion of the specimen retrieval device shown in FIG. 8 with the specimen bag deployed and the mouth of the specimen bag closed.
Figure 10:
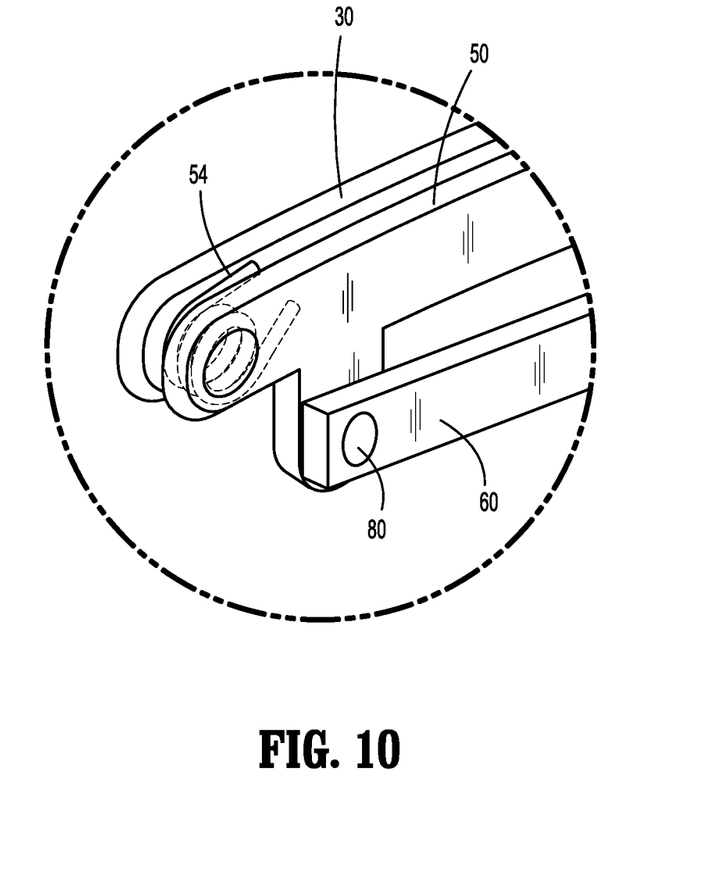
FIG. 10 is an enlarged view of the indicated area of detail shown in FIG. 9.

As depicted in FIGS. 8-10, pulling the linkage rod 41 in a proximal direction (indicated by arrows "B" in FIG. 8), retracts the linkage bars 60, 62 in a proximal direction (indicated by arrows "D" in FIG. 9), thereby allowing the first and second springs 54, 58 to relax so as to permit the band 50 to pivot in a proximal direction (indicated by arrows "C" in FIGS. 8 and 9) to close the mouth 72 (FIG. 7) of the specimen bag 70. FIG. 10 shows the connection of the spring 54 (in phantom), between the resilient finger 30 and the band 50, as well as the connection of the band 50 to the linkage bar 60 by retention pin 80.

Figure 11:
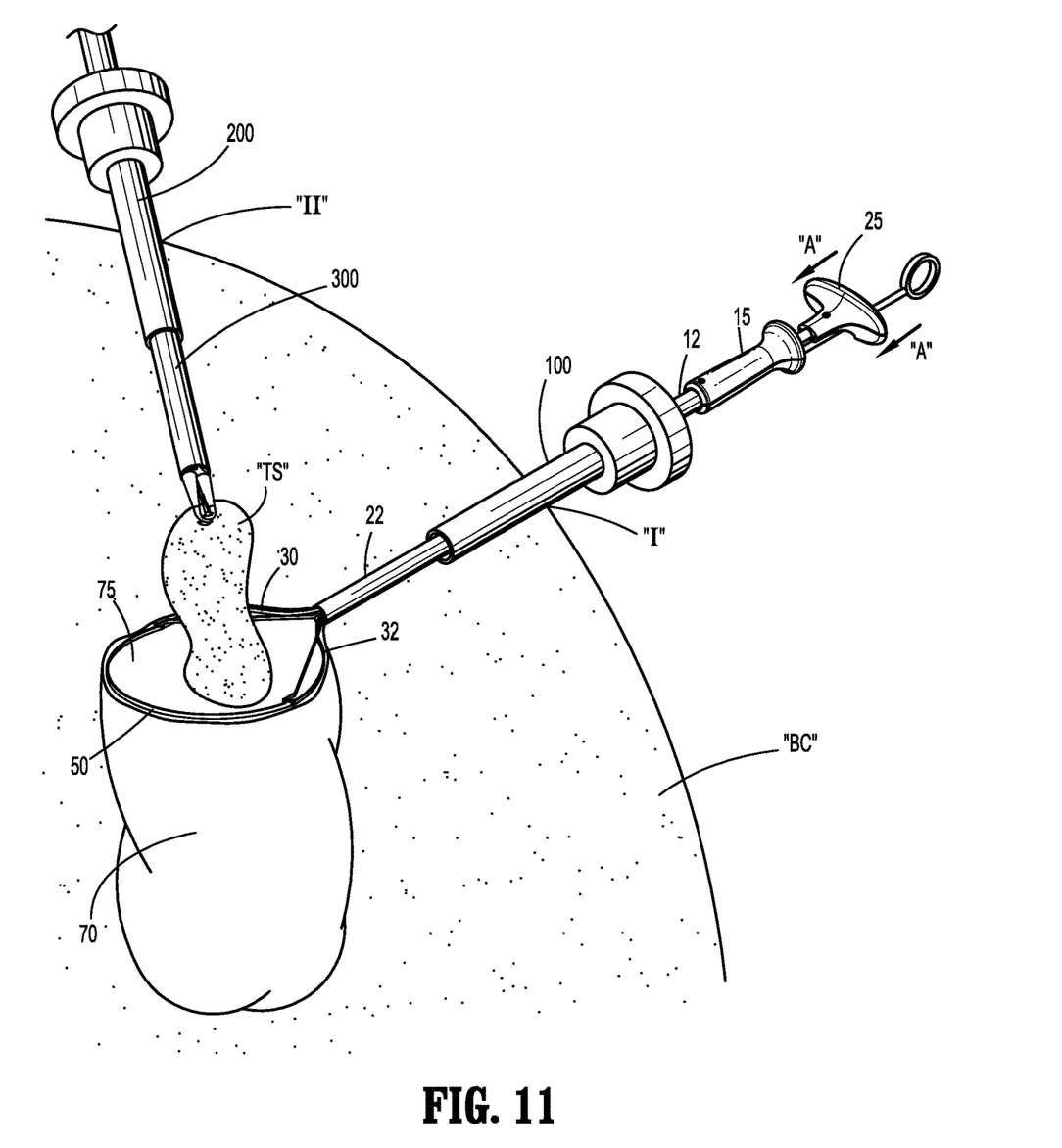
FIG. 11 is a side perspective view of the specimen retrieval device shown in FIG. 1 in use with the mouth of the specimen bag open.
Figure 12:
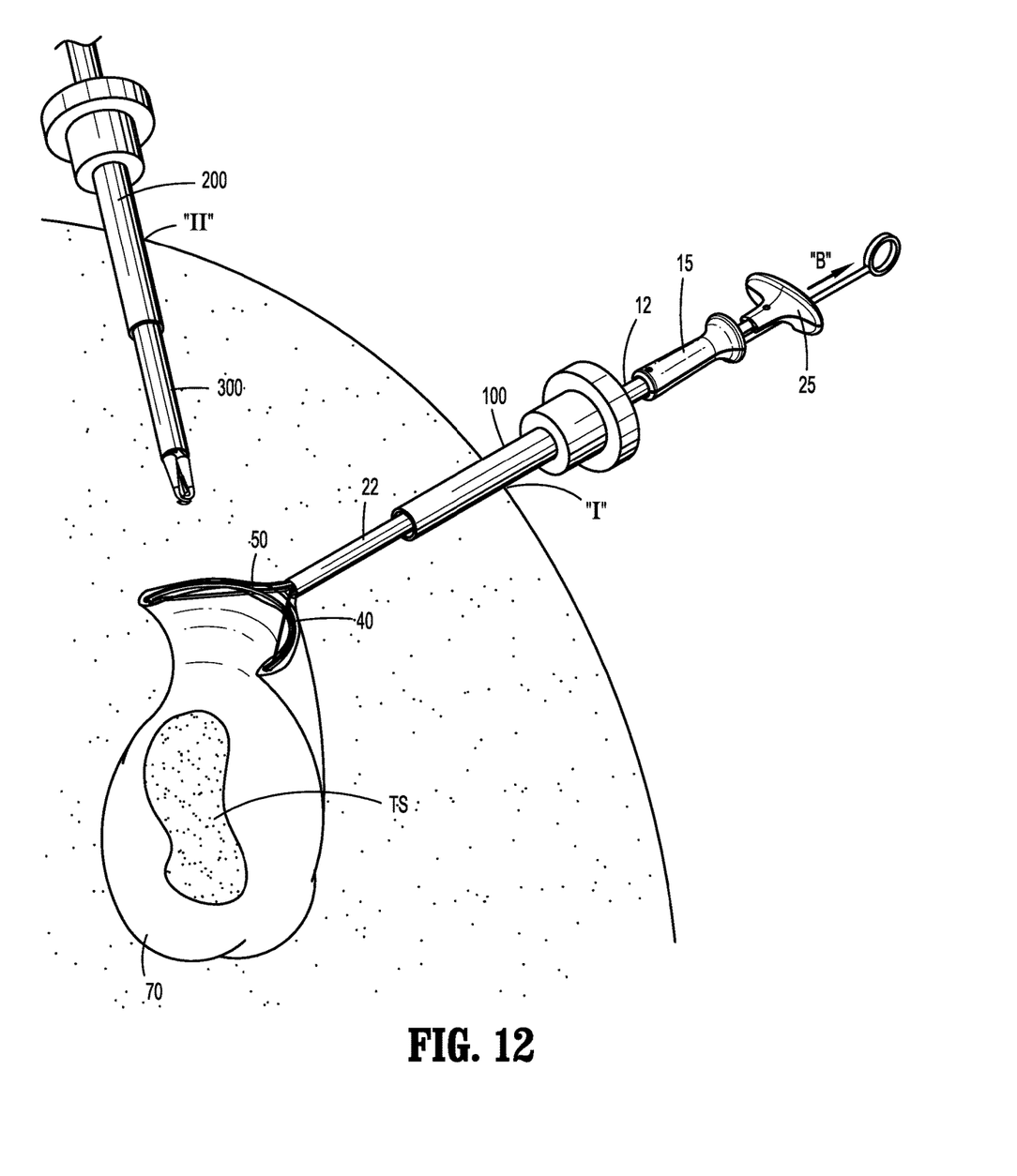
FIG. 12 is a side perspective view of the specimen retrieval device shown in FIG. 11 with the mouth of the specimen bag closed.

As depicted in FIGS. 11 and 12, in use, as depicted in FIG. 3, a first cannula 100 may be introduced through a first incision "I" for access to a patient's body cavity "BC". The tubular body 12 of the specimen retrieval device 10 can be inserted through the first cannula 100 and the inner shaft 22 deployed through the tubular body 12 by distally pushing the actuation handle 25 (indicated by arrows "A" in FIG. 11) to position the specimen bag 70 into the body cavity "BC" adjacent a surgical site. Once present within the body cavity "BC", the resilient fingers 30, 32 open to their non-deformed state, thereby forming the opening 75 of the specimen bag 70.

As shown in FIG. 11, a second cannula 200 may be introduced through a second incision "II", and a grasping device 300 (e.g., a tenaculum, forceps, etc.) may be used to place a tissue specimen "TS" into the specimen bag 70.

As shown in FIG. 12, after the tissue specimen "TS" has been placed in the specimen bag 70, pulling the linkage rod 41 in a proximal direction (indicated by arrow "B" in FIG. 12), retracts the linkage assembly 40, thereby allowing the band 50 (indicated by arrows "C" in FIGS. 8 and 9) to pivot and close the mouth 72 of the specimen bag 70.

Kits of the present disclosure may include both the specimen retrieval device described above, as well as trocars, graspers, vacuum sources (tubes), combinations thereof, and the like. In some embodiments, these additional devices, such as graspers and/or vacuum sources, may be used to break up the tissue specimen in the specimen bag prior to removing the specimen retrieval device from the body cavity.

Once the specimen retrieval device of the present disclosure has been removed from the patient's body, any tissue specimen "TS" may be removed from the specimen bag 40 for further examination and the specimen bag 40 may be discarded.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto. Additionally, it is envisioned that the elements and features illustrated or described in connection with one exemplary embodiment may be combined with the elements and features of another without departing from the scope of the present disclosure, and that such modifications and variations are also intended to be included within the scope of the present disclosure. Accordingly, the invention is not to be limited by what has been particularly shown and described, except as indicated by the appended claims.

What is claimed is:

1. A specimen retrieval device, comprising:
    a tubular body defining a longitudinal bore, the tubular body having a proximal portion, a distal portion, and a hand grip supported on the proximal portion of the tubular body;
    an inner shaft having a proximal portion, a distal portion, an actuation handle supported on the proximal portion of the inner shaft, and a support member extending from a distal portion of the inner shaft;
    a specimen bag supported on the support member at the distal portion of the inner shaft, the specimen bag including a body defining an opening that is opened and closed by a band adjacent at least a portion of the opening; and
    a linkage assembly including a linkage rod having a proximal portion, a distal portion, a longitudinal body that extends between the proximal portion and the distal portion, and a pair of linkage bars extending from the distal portion of the longitudinal body of the linkage rod, the pair of linkage bars each attached to the band adjacent at least a portion of the opening by biasing means rotatable around an axis transverse to the specimen bag, the biasing means pivoting the band adjacent at least a portion of the opening to close the opening when the linkage rod is moved in a closing direction.

2. The specimen retrieval device of claim 1, wherein the support member includes a pair of resilient fingers which support the specimen bag and open the open end of the specimen bag in a deployed state.

3. The specimen retrieval device of claim 2, wherein the resilient fingers are positioned adjacent the open end of the specimen bag to open the specimen bag when the specimen retrieval device is in the deployed state.

4. The specimen retrieval device of claim 1, wherein the specimen bag is furled about the inner shaft in a non-deployed state.

5. The specimen retrieval device of claim 1, wherein the biasing means include torsion springs.

6. The specimen retrieval device of claim 1, wherein moving the linkage rod in a closing direction includes proximally pulling the linkage rod.

7. The specimen retrieval device of claim 1, wherein the proximal portion of the linkage rod has a ring configuration.

8. The specimen retrieval device of claim 1, wherein the linkage rod extends proximally from the tubular body.

9. The specimen retrieval device of claim 1, wherein the proximal portion of each of the inner shaft and the linkage rod extends proximally from the tubular body.

10. A method comprising:
    introducing the tubular body of the specimen retrieval device of claim 1 through a body opening into a body cavity;
    introducing the inner shaft of the specimen retrieval device through the longitudinal bore of the tubular body;
    introducing the linkage rod of the specimen retrieval device through the longitudinal bore of the tubular body;
    moving the inner shaft including the support member within the longitudinal bore of the tubular body to position the specimen bag supported on the support member within the body cavity;
    placing a tissue specimen into the specimen bag through an opening of the specimen bag;
    moving the linkage rod of the linkage assembly, the linkage assembly adjacent the opening of the specimen bag, to permit the biasing means connecting the linkage assembly to the band adjacent the opening of the specimen bag to close the opening of the specimen bag within the body cavity; and
    removing the specimen retrieval device from the body cavity.

11. The method of claim 10, further including breaking up the tissue specimen in the specimen bag prior to removing the specimen retrieval device from the body cavity.

12. The method of claim 10, wherein moving the linkage rod occurs by proximally pulling the linkage rod.

* * * * *